United States Patent
Godwin et al.

(10) Patent No.: US 9,650,331 B2
(45) Date of Patent: May 16, 2017

(54) CONJUGATION REAGENTS

(71) Applicant: POLYTHERICS LIMITED, London (GB)

(72) Inventors: Antony Godwin, London (GB); Stephen Brocchini, London (GB)

(73) Assignee: POLYTHERICS LIMITED, London (GB)

(*) Notice: Subject to any disclaimer, the term of this patent is extended or adjusted under 35 U.S.C. 154(b) by 0 days.

(21) Appl. No.: 13/919,217

(22) Filed: Jun. 17, 2013

(65) Prior Publication Data

US 2013/0338231 A1    Dec. 19, 2013

Related U.S. Application Data

(60) Provisional application No. 61/661,300, filed on Jun. 18, 2012, provisional application No. 61/720,811, filed on Oct. 31, 2012.

(51) Int. Cl.
| | | |
|---|---|---|
| *A61K 31/17* | (2006.01) | |
| *C07C 317/50* | (2006.01) | |
| *C07C 315/04* | (2006.01) | |
| *C08G 65/333* | (2006.01) | |
| *C08G 65/334* | (2006.01) | |

(52) U.S. Cl.
CPC .......... *C07C 317/50* (2013.01); *C07C 315/04* (2013.01); *C08G 65/3348* (2013.01); *C08G 65/33334* (2013.01); *C08G 65/33396* (2013.01); *C08G 2650/50* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 5,932,462 | A | 8/1999 | Harris et al. |
| 7,595,292 | B2 | 9/2009 | Brocchini et al. |
| 7,786,221 | B2 | 8/2010 | Harris et al. |
| 7,939,630 | B2 | 5/2011 | Brocchini et al. |
| 8,354,477 | B2 | 1/2013 | Harris et al. |
| 2010/0239517 | A1 | 9/2010 | Brocchini et al. |
| 2011/0136723 | A1 | 6/2011 | Godwin |
| 2011/0182855 | A1 | 7/2011 | Brocchini et al. |
| 2011/0262994 | A1 | 10/2011 | Godwin |
| 2012/0014905 | A1 | 1/2012 | Godwin et al. |
| 2012/0115772 | A1 | 5/2012 | Choi et al. |

FOREIGN PATENT DOCUMENTS

| | | |
|---|---|---|
| EP | 1 932 855 | 6/2008 |
| WO | 2005/007197 | 1/2005 |
| WO | 2006/134148 | 12/2006 |
| WO | 2010/057962 | 5/2010 |
| WO | 2011/077067 | 6/2011 |
| WO | WO 2011077067 A1 * | 6/2011 |
| WO | 2011/146518 | 11/2011 |

OTHER PUBLICATIONS

Cong et al (Bioconjugate Biochem 23:248-263, 2012).*
Balan et al. "Site-specific PEGylation of protein disulfide bonds using a three-carbon bridge" *Bioconjugate Chemistry* 18:61-76 (Jan.-Feb. 2007).
Brocchini et al. "Disulfide bridge based PEGylation of proteins" *Advanced Drug Delivery Reviews* 60:3-12 (Jan. 2008).
Carmali et al. "Synthetic studies to prepare PEG-glutamic acid analogues" poster and abstract for UKICRS Symposium (Apr. 2010).
Carmali et al. "Synthesis of branched bis-alkylation PEG reagents" poster and abstract for RSC Conference (Nov. 2011).
Cong et al. "Site-specific PEGylation at histidine tags" *Bioconjugate Chemistry* 23:248-263 (Feb. 2012).
Elliott et al. "Evidence for metabolic cleavage of a PEGylated protein in vivo using multiple analytical methodologies" *Molecular Pharmaceutics* 9:1291-1301 (May 2012).
Lewis et al. "Poly(2-methacryloyloxyethyl phosphorylcholine) for protein conjugation" *Bioconjugate Chemistry* 19:2144-2155 (Nov. 2008).
Roberts et al. "Chemistry for peptide and protein PEGylation" *Advanced Drug Delivery Reviews* 54:459-476 (Jun. 2002).

* cited by examiner

*Primary Examiner* — Craig Ricci
(74) *Attorney, Agent, or Firm* — Nixon & Vanderhye PC

(57) ABSTRACT

The invention provides compound of the general formula:

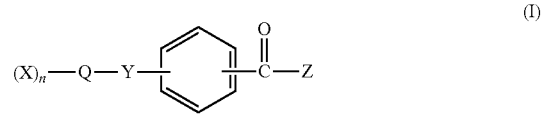

(I)

in which each X independently represents a polymer chain; n represents an integer greater than 1; Q represents a linker; Y represents an amide group; and Z represents either —CH($CH_2L$)$_2$ or —C($CH_2L$)(=$CH_2$), in which each L independently represents a leaving group. The compounds are useful reagents for the conjugation of polymers to proteins, the resulting conjugates being novel and also forming part of the invention.

6 Claims, 3 Drawing Sheets

CONJUGATION REAGENTS

This application claims priority benefit of provisional U.S. Application No. 61/661,300, filed Jun. 18, 2012, and provisional U.S. Application No. 61/720,811, filed Oct. 31, 2012; the contents of each of which are incorporated in their entirety by reference herein.

This invention relates to novel conjugation reagents for conjugating polymers to proteins and peptides, and to a novel process for producing novel conjugates.

Many therapeutically active molecules, for example proteins, do not possess the properties required to achieve efficacy in clinical medical use. For example, many native proteins do not make good medicines because upon administration to patients there are several inherent drawbacks that include: (1) proteins are digested by many endo- and exo-peptidases present in blood or tissue; (2) almost all proteins are immunogenic to some extent; and (3) proteins can be rapidly excreted by kidney ultrafiltration and by endocytosis. Some molecules which might find utility as active therapeutic agents in medicines are systemically toxic or lack optimal bioavailability and pharmacokinetics. When proteins clear from the blood circulation quickly they typically have to be administered to the patient frequently. Frequent administration further increases the risk of toxicity, especially immunologically derived toxicities. Often it is difficult to achieve a therapeutically effective dose, so efficacy is compromised. Rapid clearance is therefore both an efficacy issue and a safety issue.

Water soluble, synthetic polymers, particularly polyalkylene glycols, are widely used to conjugate therapeutically active molecules such as proteins. These therapeutic conjugates have been shown to alter pharmacokinetics favourably by prolonging circulation time and decreasing clearance rates, decreasing systemic toxicity, and in several cases, displaying increased clinical efficacy. The process of covalently conjugating polyethylene glycol, PEG, to proteins is commonly known as "PEGylation".

It is important for optimised efficacy and to ensure dose to dose consistency that the number of conjugated polymer molecules per protein is the same for each molecule, and that each polymer molecule is specifically covalently conjugated to the same amino acid residue in each protein molecule. Non-specific conjugation at sites along a protein molecule results in a distribution of conjugation products and, frequently, unconjugated protein, to give a complex mixture that is difficult and expensive to purify.

WO 2005/007197 describes a series of novel conjugation reagents which can be used to react with nucleophilic groups in a protein to produce a protein-polymer conjugate. These reagents find particular utility for their ability to conjugate with both sulfur atoms derived from a disulfide bond in a protein to give thioether conjugates, and can also be used to conjugate with other nucleophiles, for example with two histidine residues, for example two histidine residues present in a polyhistidine tag attached to a protein, as described in WO 2009/047500.

For some uses, it is desirable to conjugate two polymer chains to a protein, because the steric properties of a conjugate containing a single chain of a given molecular weight can be significantly different from the properties of a conjugate containing, for example, two chains each having half that molecular weight. Reagents capable of such conjugation are known. Thus for example U.S. Pat. No. 5,932,462 (Harris) discloses reagents capable of conjugating two PEG chains to proteins. Cong et al., Bioconjugate Chemistry 23 (2012) 248-263, also discloses a reagent capable of conjugating two PEG chains to proteins, specifically, the PEG-bis-sulfone reagent shown as reagent 3 of FIG. 1, p. 249. In Cong's reagent, two PEG chains are attached to different positions on a phenyl group acting as a linker to the functional protein reacting group of the reagent. Cong's reagent is capable of conjugation of two PEG chains to, for example, two sulfur atoms derived from a disulfide bond in a protein, or two histidine residues present in a polyhistidine tag attached to a protein, which provides improved conjugation compared with the reagents of Harris.

We have now found a novel reagent capable of conjugating two polymer chains to a protein, which shows improved properties over the known reagent of Cong.

Accordingly, the present invention provides a compound of the general formula:

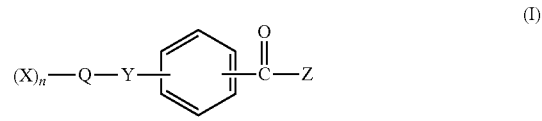

(I)

in which each X independently represents a polymer chain; n represents an integer greater than 1; Q represents a linker; Y represents an amide group; and Z represents either —CH.(CH$_2$L)$_2$ or —C(CH$_2$L)(=CH$_2$), in which each L independently represents a leaving group.

The reagents of the formula I contain at least two polymer chains X, each linked to linker Q. Each polymer X may for example be a poly(alkylene glycol), a polyvinylpyrrolidone, a polyacrylate, for example poly(acryloyl morpholine), a polymethacrylate, a polyoxazoline, a polyvinylalcohol, a polyacrylamide or polymethacrylamide, for example polycarboxymethacrylamide, or a HPMA copolymer. Additionally the polymer may be one that is susceptible to enzymatic or hydrolytic degradation. Such polymers, for example, include polyesters, polyacetals, poly(ortho esters), polycarbonates, poly(imino carbonates), and polyamides, such as poly(amino acids). A polymer may be a homopolymer, random copolymer or a structurally defined copolymer such as a block copolymer. For example it may be a copolymer, e.g., a block copolymer, derived from two or more alkylene oxides, or from poly(alkylene oxide) and either a polyester, polyacetal, poly(ortho ester), or a poly(amino acid). The so-called Pluronics are an important class of PEG block copolymers. These are derived from ethylene oxide and propylene oxide blocks. Polyfunctional polymers that may be used include copolymers of divinylether-maleic anhydride and styrene-maleic anhydride.

Naturally occurring polymers may also be used, for example polysaccharides such as chitin, dextran, dextrin, chitosan, starch, cellulose, glycogen, poly(sialylic acid) and derivatives thereof. A protein may be used as the polymer. This allows conjugation of one protein, for example an antibody or antibody fragment, to a second protein, for example an enzyme or other active protein. Also, if a peptide containing a catalytic sequence is used, for example an O-glycan acceptor site for glycosyltransferase, it allows the incorporation of a substrate or a target for subsequent enzymatic reaction. Poly(amino acid)s such as polyglutamic acid or polyglycine may also be used, as may hybrid polymers derived from natural monomers such as saccharides or amino acids and synthetic monomers such as ethylene oxide or methacrylic acid.

Preferably each polymer used in the present invention is a hydrophilic or water-soluble, synthetic polymer. If a polymer is a poly(alkylene glycol), this is preferably one containing $C_2$ and/or $C_3$ units, and is especially a poly(ethylene glycol) (PEG). Except where the context requires otherwise, any reference to a polymer in this specification should be understood to include a specific reference to PEG.

A polymer may optionally be derivatised or functionalised in any desired way. Reactive groups may be linked at the polymer terminus or end group, or along the polymer chain through pendent linkers; in such cases, the polymer is for example a polyacrylamide, polymethacrylamide, polyacrylate, polymethacrylate, or a maleic anhydride copolymer. Such functionalised polymers provide a further opportunity for preparing multimeric conjugates (i.e., conjugates in which the polymer is conjugated to more than one molecule). For example, a polymer may carry one or more drug molecules at any point along its length, for example at its terminus. If desired, the polymer may be coupled to a solid support using conventional methods.

The two or more polymer chains X may be the same or different. Specifically, each X may represent the same chemical polymer, or a different chemical polymer. For example, each X may represent a PEG chain, or one X may represent a PEG chain and another X may represent a different polymer, for example a PVP or a protein chain.

Each polymer X may contain a single linear chain, or it may have branched morphology composed of many chains either small or large. Generally, a polymer chain is initiated or terminated by a suitable end group, and is connected at the other end of the chain to the linker group Q: for example, a PEG chain may have an end group selected from alkoxy, e.g., methoxy, aryloxy, carboxy or hydroxyl. Where the chain is branched, each free branch terminus will carry the end group. When preparing the reagents of the invention, the other end of the polymer X will be reacted with a compound containing the linker Q, and the nature of this linkage depends upon chemical convenience. For example, when the polymer is PEG, the terminal —OH group may be reacted with a suitable complementary group on Q. Alternatively, as is well known in the art, the PEG can be converted to the PEG amine, PEG-NH$_2$, which tends to be more reactive than PEG alcohol, before reaction with a suitable complementary group on Q. Thus, some PEG-containing reagents according to the invention will include an oxygen atom linking PEG to Q, while others will include an NH group linking PEG to Q, for example CH$_3$O—(CH$_2$CH$_2$O)$_m$— or CH$_3$O—(CH$_2$CH$_2$O)$_{m-1}$(CH$_2$CH$_2$NH)— in which m is the number of ethylene oxide units in the PEG, and in which the end group is shown as methoxy for convenience.

Each polymer chain X may have any suitable molecular weight, and each polymer chain X may have the same or different molecular weight as any other. For example each chain may have a molecular weight of at least 5, 10, 15, 20, 30, or 40 kDa. Generally, the preferred maximum molecular weight of each chain is 60 kDa. When a conjugate is intended to leave the circulation and penetrate tissue, for example for use in the treatment of inflammation caused by malignancy, infection or autoimmune disease, or by trauma, it may be advantageous to use a conjugate in which the total molecular weight of the polymers $(X)_n$ is in the range 2000-30,000 g/mol. For applications where the conjugate is intended to remain in circulation it may be advantageous to use a higher total molecular weight of polymer, for example in the range of 20,000-75,000 g/mol.

n must be greater than 1, for example up to 4, for example 2 or 3. Reagents and conjugates in which n is 2 are particularly preferred.

The reagents of the present invention contain an amide group, Y, which as drawn in the formula I may be —CO—NR'— or, preferably, —NR'—CO—, in which R' represents a $C_{1-4}$alkyl group, for example a methyl group, or, especially, a hydrogen atom. This group may be linked to the phenyl group shown in formula I at any position, but is preferably in the para position relative to the —CO.Z group. The phenyl group of the formula I may carry additional substituents if desired, but is preferably unsubstituted.

In order to carry more than one polymer chain, the linker must contain at least one branching atom, generally a carbon or a nitrogen atom. Where the branching atom is a carbon atom, a linking group Q may for example be an alkylene group (preferably a $C_{1-10}$ alkylene group) or an optionally-substituted aryl (for example phenyl) or heteroaryl group, any of which may be terminated or interrupted and/or terminated by one or more oxygen atoms, sulfur atoms, —NR groups (in which R represents a hydrogen atom or an alkyl (preferably $C_{1-6}$alkyl), aryl (preferably phenyl), or alkyl-aryl (preferably $C_{1-6}$alkyl-phenyl) group), keto groups, —O—CO— groups, —CO—O— groups, —O—CO—O, —O—CO—NR—, —NR—CO—O—, —CO—NR— and/or —NR.CO— groups. Preferably the linker is a $C_{1-10}$ alkylene group, especially a $C_{1-6}$ alkylene group, interrupted and/or terminated by one or more oxygen atoms and/or NH groups and/or keto groups, especially a $C_{1-6}$alkylene group interrupted by an oxygen atom. An especially preferred reagent of the formula I contains a linker group Q of formula:

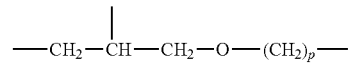

in which p is 1 to 6, for example 1, 2 or, especially, 3.

Another specific group of reagents of the formula I contains a linker group Q of formula:

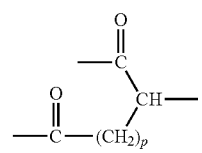

in which p has the meaning given above. When p is 1, this linker is derived from aspartic acid, and when p is 2, this linker is derived from glutamic acid.

In another embodiment of the invention, the branching atom may be nitrogen, and the linker may be one of those mentioned above in which the branching carbon atom is replaced by a branching nitrogen atom. For example, in one specific embodiment of the invention, the linker may be of the formula:

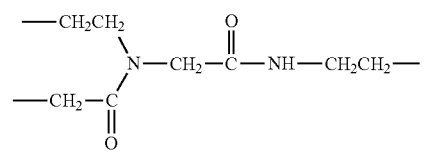

where a linker group Q is terminated adjacent the amide group Y by an oxygen atom or an NH group, then the combination of this terminating group and Y forms a urethane or urea group —O—CO—NR'— or —NH—CO—NR'—.

The linkage via the linker Q to the polymer may be by way of a hydrolytically labile bond, or by a non-labile bond.

A leaving group L may for example represent —SR, —SO₂R, —OSO₂R, —N⁺R₃, —N⁺HR₂, —N⁺H₂R, halogen, or —OØ, in which R has the meaning given above, and Ø represents a substituted aryl, especially phenyl, group, containing at least one electron withdrawing substituent, for example —CN, —NO₂, —CO₂R, —COH, —CH₂OH, —COR, —OR, —OCOR, —OCO₂R, —SR, —SOR, —SO₂R, —NHCOR, —NRCOR, —NHCO₂R, —NRCO₂R, —NO, —NHOH, —NROH, —C=N—NHCOR, —C=N—NRCOR, —N⁺R₃, —N⁺HR₂, —N⁺H₂R, halogen, for example chlorine or, especially, bromine or iodine, —C≡CR, —C=CR₂ and —C=CHR, in which each R independently has one of the meanings given above. Alkyl or aryl sulfonyl groups are particularly preferred leaving groups, with phenylsulfonyl or, especially, tosyl, being especially preferred. Where two Ls are present, these may be different groups, but preferably they are the same group.

Except where otherwise stated, substituents which may be present on any optionally substituted aryl, for example phenyl, or heteroaryl group present in a compound of formula I include for example one or more of the same or different substituents selected from alkyl (preferably $C_{1-4}$alkyl, especially methyl, optionally substituted by OH or CO₂H), —CN, —NO₂, —CO₂R, —COH, —CH₂OH, —COR, —OR, —OCOR, —OCO₂R, —SR, —SOR, —SO₂R, —NHCOR, —NRCOR, NHCO₂R, —NR.CO₂R, —NO, —NHOH, —NR.OH, —C=N—NHCOR, —C=N—NR.COR, —N⁺R₃, —N⁺H₃, —N⁺HR₂, —N⁺H₂R, halogen, for example fluorine or chlorine, —C≡CR, —C=CR₂ and —C=CHR, in which each R independently has one of the meanings given above. Preferred substituents, if present, include for example CN, NO₂, —OR, —OCOR, —SR, —NHCOR, —NR.COR, —NHOH and —NR.COR.

Especially preferred reagents according to the invention have the formulae:

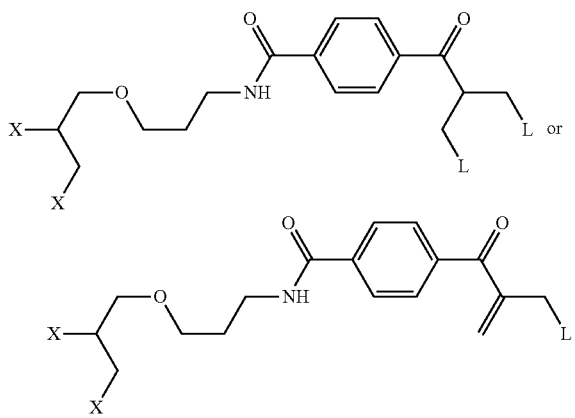

In these reagents, preferably X is polyethylene glycol, especially methoxy-terminated polyethylene glycol, i.e., CH₃O—(CH₂CH₂O)ₘ— in which m is the number of ethylene oxide units in the PEG. In addition, in these reagents, preferably each L is a tosyl group, thus:

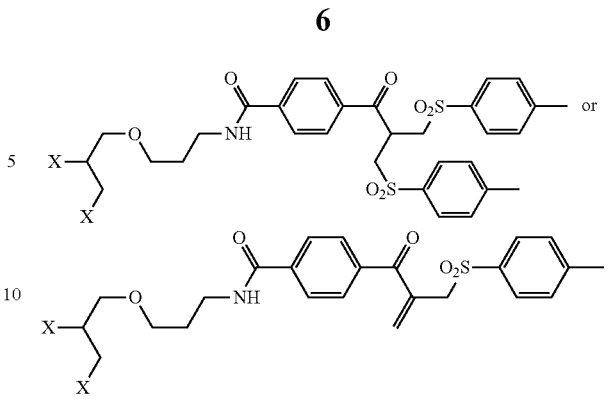

The compounds of formula I may be used for conjugation to a protein or peptide. For convenience, the term "protein" will be used throughout this Specification, and except where the context requires otherwise, the use of the term "protein" should be understood to include a reference to peptide.

Accordingly, the invention further provides a process for the preparation of a polymer conjugate, which comprises reacting a compound of the general formula I with a protein or a peptide. The resulting conjugates have the general formula:

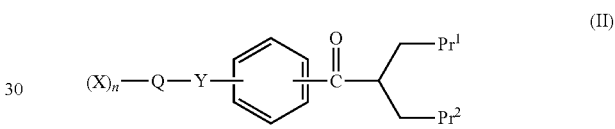

in which X, n, Q and Y have the meanings given above, and either each of Pr¹ and Pr² represents a separate protein or peptide molecule, or Pr¹ and Pr² together represent a single protein or peptide Pr bonded at two separate points, thus:

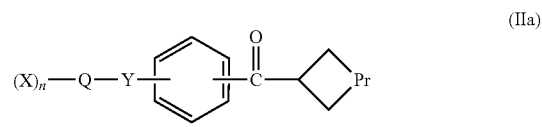

Preferably Pr¹ and Pr² together represent a single protein bonded to two sulfur atoms derived from a disulfide bond in a protein, or to two histidine residues present in a polyhistidine tag attached to a protein (i.e., the resulting conjugates have the general formula IV(a)).

In the reagent of formula I, Z represents either —CH.(CH₂L)₂ or —C(CH₂L)(=CH₂). These two groups are chemically equivalent to each other. If a reagent of formula I in which Z represents —CH.(CH₂L)₂, i.e., a reagent of formula Ia:

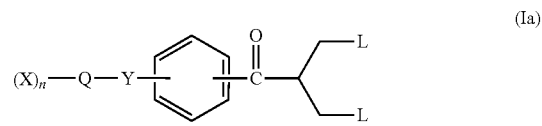

is used to react with a protein in a process according to the invention, the reaction proceeds by the loss of one leaving group L, and resultant formation of a reagent of formula I in which Z represents —C(CH₂L)(=CH₂), i.e., a reagent of formula Ib:

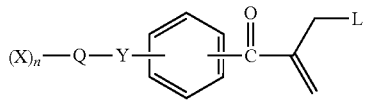 (Ib)

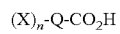

This reagent reacts with one nucleophile, for example a cysteine, histidine or lysine residue, in the protein. Subsequently, the remaining leaving group L is lost, and reaction with a second nucleophile (either in a second molecule of protein or in the same protein molecule as the first nucleophile) occurs to form the desired conjugate. Therefore, the process of the invention can be carried out using a compound of formula Ia as a starting material, in which case a compound of formula Ib is formed in situ, or a pre-formed compound of formula Ib may be used as starting material.

The conjugation reaction according to the invention may be carried out under the reaction conditions described in WO 2005/007197 and WO 2009/047500. The process may for example be carried out in a solvent or solvent mixture in which all reactants are soluble. For example, the protein may be allowed to react directly with the polymer conjugation reagent in an aqueous reaction medium. This reaction medium may also be buffered, depending on the pH requirements of the nucleophile. The optimum pH for the reaction will generally be at least 4.5, typically between about 5.0 and about 8.5, preferably about 6.0 to 7.5. The optimal reaction conditions will of course depend upon the specific reactants employed.

Reaction temperatures between 3-37° C. are generally suitable when using an aqueous reaction medium. Reactions conducted in organic media (for example THF, ethyl acetate, acetone) are typically conducted at temperatures up to ambient.

Where bonding to the protein is via two sulfur atoms derived from a disulfide bond in the protein, the process may be carried out by reducing the disulfide bond in situ following which the reduced product reacts with the reagent of the formula I. Preferably the disulfide bond is reduced and any excess reducing agent is removed, for example by buffer exchange, before the conjugation reagent is introduced. The disulfide can be reduced, for example, with dithiothreitol, mercaptoethanol, or tris-carboxyethylphosphine using conventional methods.

The protein can be effectively conjugated using a stoichiometric equivalent or a slight excess of conjugation reagent I. However, it is also possible to conduct the conjugation reaction with an excess stoichiometry of conjugation reagent, and this may be desirable for some proteins. The excess reagent can easily be removed, for example by ion exchange chromatography, during subsequent purification of the conjugate.

Compounds of the general formula I in which Z represents —CH.(CH$_2$L)$_2$ may be prepared by either reacting a compound of the general formula I (X)$_n$-Q-NH$_2$ (III)

with a compound of the general formula

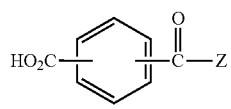 (IV)

or by reacting a compound of the general formula (X)$_n$-Q-CO$_2$H (V)

with a compound of the general formula

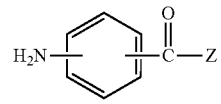 (VI)

In both cases, an amide group is formed. As is well known in the art, the CO$_2$H group which is reacted to form the amide group, is suitably activated to facilitate the reaction, for example by formation of an active ester, an acyl chloride, or an anhydride, or directly with amine by the use of an activation agent such as a carbodiimide.

As explained above, compounds of the general formula I in which Z represents —C(CH$_2$L)(=CH$_2$) may be prepared by removing a leaving group L from the corresponding compound of the general formula I in which Z represents a —CH.(CH$_2$L)$_2$ group.

The immediate product of the process according to the invention is a conjugate which still contains the keto group CO attached to the phenyl ring in formula I, i.e., a conjugate of formula II, especially IIa, above. However, the process of the invention is reversible under suitable conditions. This may be desirable for some applications, for example where rapid release of the protein is required, but for other applications, rapid release of the protein may be undesirable. It may therefore be desirable to stabilise the conjugates by reduction of the keto group to give a moiety which prevents release of the protein, typically a hydroxyl group OH, although reductive amination is also a possibility, giving an amine group CH.NH$_2$, CH.NHR or CH.NR$_2$ in which each R independently has the meaning given above. These groups may be further reacted if desired, for example a hydroxy group may be converted into an ether group CH.OR by reaction with an etherifying agent; an ester group CH.O.C(O)R may be obtained by the reaction of a hydroxy group with an acylating agent; or an amide CH.NHC(O)R or CH.N(C(O)R)$_2$ may be formed by acylation of an amine. Accordingly, the process according to the invention may comprise the additional step of reducing the keto group in the conjugate. The use of a borohydride, for example sodium borohydride, sodium cyanoborohydride, potassium borohydride or sodium triacetoxyborohydride, as reducing agent is particularly preferred. Other reducing agents which may be used include for example tin(II) chloride, alkoxides such as aluminium alkoxide, and lithium aluminium hydride.

Conjugates preparable by the process of the present invention are novel, and therefore form part of the present invention per se. Novel conjugates according to the present invention have the general formula:

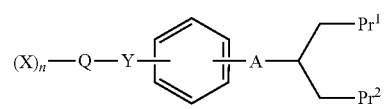 IIb in which X, n, Q and Y have the meanings given above, A represent a group CO, CHOH, CH.NH$_2$, CH.NHR, CH.NR$_2$, CH.OR CH.O.C(O)R, CH.NHC(O)R, or CH.N(C(O)R)$_2$, in which each R has the meaning given above, and either each of Pr[1] and Pr[2] represents a separate protein or peptide molecule or both of Pr[1] and Pr[2] together represent a single protein or peptide bonded at two separate points. Preferred conjugates have the general formula:

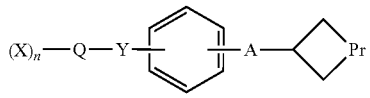
IIc in which X, n, Q, Y and A have the meanings given above, and Pr represents a single protein or peptide bonded at two separate points.

Especially preferred conjugates are of the formulae:

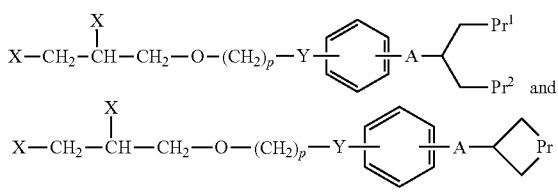

Of course, it is possible for more than one conjugating reagent of the formula I to be conjugated to a protein, where the protein contains sufficient suitable attachment points. For example, in a protein which contains two different disulfide bonds, or in a protein which contains one disulfide bond and also carries a polyhistidine tag, it is possible to conjugate two molecules of the reagent of formula I per molecule of protein.

Suitable proteins which may be conjugated using the process of the invention include for example peptides, polypeptides, antibodies, antibody fragments, enzymes, cytokines, chemokines, receptors, blood factors, peptide hormones, toxin, transcription proteins, or multimeric proteins.

The following gives some specific proteins which may be conjugated using the present invention. Enzymes include carbohydrate-specific enzymes, proteolytic enzymes and the like, for example the oxidoreductases, transferases, hydrolases, lyases, isomerases and ligases disclosed by U.S. Pat. No. 4,179,337. Specific enzymes of interest include asparaginase, arginase, adenosine deaminase, superoxide dismutase, catalase, chymotrypsin, lipase, uricase, bilirubin oxidase, glucose oxidase, glucuronidase, galactosidase, glucocerebrosidase, glucuronidase, and glutaminase.

Blood proteins include albumin, transferrin, Factor VII, Factor VIII or Factor IX, von Willebrand factor, insulin, ACTH, glucagen, somatostatin, somatotropins, thymosin, parathyroid hormone, pigmentary hormones, somatomedins, erythropoietin, luteinizing hormone, hypothalamic releasing factors, antidiuretic hormones, prolactin, interleukins, interferons, for example IFN-α or IFN-β, colony stimulating factors, hemoglobin, cytokines, antibodies, antibody fragments, chorionicgonadotropin, follicle-stimulating hormone, thyroid stimulating hormone and tissue plasminogen activator.

Other proteins of interest are allergen proteins disclosed by Dreborg et al., Crit. Rev. Therap. Drug Carrier Syst. 6 (1990) 315-365 as having reduced allergenicity when conjugated with a polymer such as poly(alkylene oxide) and consequently are suitable for use as tolerance inducers. Among the allergens disclosed are Ragweed antigen E, honeybee venom, mite allergen and the like.

Glycopolypeptides such as immunoglobulins, ovalbumin, lipase, glucocerebrosidase, lectins, tissue plasminogen activator and glycosilated interleukins, interferons and colony stimulating factors are of interest, as are immunoglobulins such as IgG, IgE, IgM, IgA, IgD and fragments thereof.

Of particular interest are receptor and ligand binding proteins and antibodies and antibody fragments which are used in clinical medicine for diagnostic and therapeutic purposes. The antibody may be used alone or may be covalently conjugated ("loaded") with another atom or molecule such as a radioisotope or a cytotoxic/antiinfective drug. Epitopes may be used for vaccination to produce an immunogenic polymer-protein conjugate.

Particularly preferred proteins include antibody fragments, for example IgG Fab fragment, and interferons, such as IFN-α, IFN-β and consensus IFN.

The protein may be derivatised or functionalised if desired. In particular, prior to conjugation, the protein, for example a native protein, may have been reacted with various blocking groups to protect sensitive groups thereon; or it may have been previously conjugated with one or more polymers or other molecules, either using the process of this invention or using an alternative process. In one preferred embodiment of the invention, it contains a polyhistidine tag, which can be targeted by the conjugation reagent according to the invention.

The invention further provides a pharmaceutical composition comprising a conjugate according to the invention together with a pharmaceutically acceptable carrier, and optionally also containing a further active ingredient in addition to the conjugate according to the invention; a conjugate according to the invention for use in therapy; the use of a conjugate according to the invention in a process for the manufacture of a medicament; and a method of treating a patient which comprises administering a pharmaceutically-effective amount of a conjugate or a pharmaceutical composition according to the invention to a patient.

The conjugating reagents of the present invention have been found to be extremely useful, being capable of highly efficient site-specific conjugation to proteins, the resulting novel conjugates demonstrating a high level of stability. As illustrated in the examples below, dramatically improved efficiency over the comparable known reagent of Cong et al., Bioconjugate Chemistry 23 (2012) 248-263, is obtained.

The accompanying drawings illustrate results obtained in the following Examples:

BRIEF DESCRIPTION OF THE DRAWINGS

FIG. 1 illustrates the SDS-PAGE gel obtained in Example 2.

FIGS. 2, 3 and 4 illustrate the SDS-PAGE gels obtained in Example 3.

Figure 3:
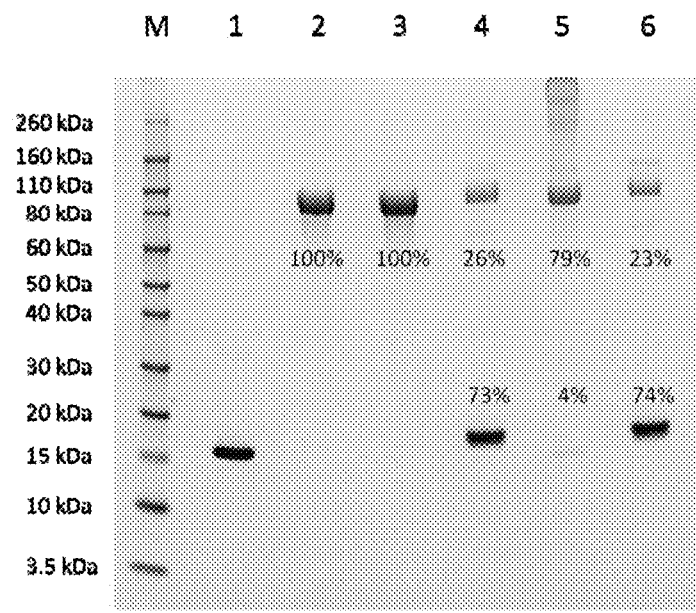

The following Examples illustrate the invention.

EXAMPLE 1

Preparation of PEG Reagent 1

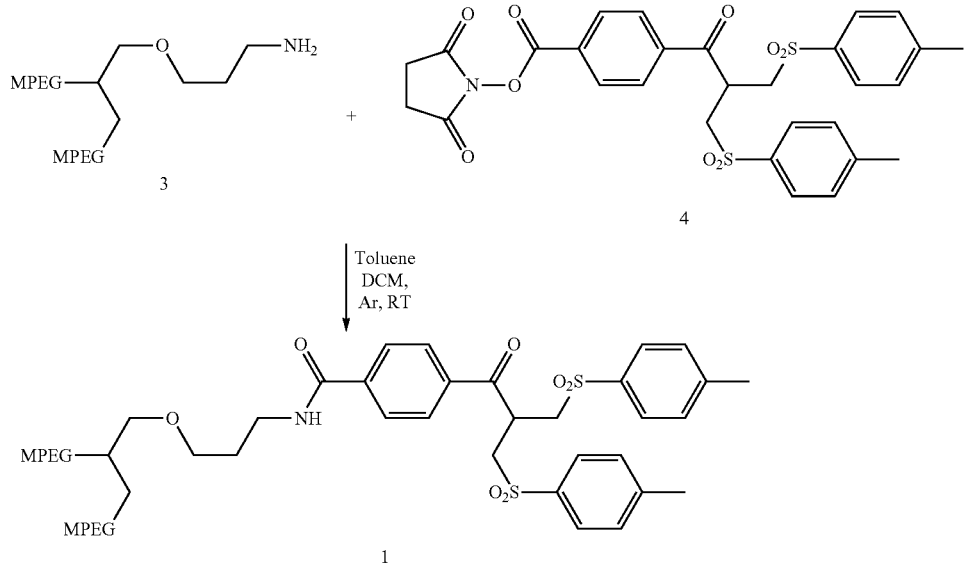

40 (2×20) kDa bifurcated PEG amine 3 (MPEG being $CH_3O.CH_2CH_2O)_m$—) was purchased from NOF CORPORATION(SUNBRIGHT GL2-400 PA, lot: M7D902). 4-[2,2-bis[(p-tolylsulfonyl)methyl]acetyl]benzoic acid-NHS ester, 4 was prepared according to Brocchini et al., Nat. Protoc. 1 (2006) 2241-2252.

To a single neck round-bottomed flask containing a magnetic stirrer bar, was added bifurcated PEG amine 3 (300 mg) and toluene (8 mL). The resulting homogeneous solution was evaporated under reduced pressure using a rotary evaporator for 2 h to leave a solid residue. The residue was dissolved in dichloromethane (15 mL), the flask was sealed with a septum and the mixture stirred under argon. To the solution was added activated linker 4 (27 mg), the flask was resealed with a septum and the reaction was stirred at rt overnight. The septum was removed and the volatile portion was removed via evaporation under reduced pressure using a rotary evaporator. Acetone (20 mL) was added to the residue and the solid was dissolved with gentle warming (30° C.). The resulting solution was filtered through non-absorbent cotton wool into a 50 mL Falcon tube. Cooling the solution in a dry-ice bath resulted in a thick precipitate. Centrifugation (−9° C., 4000 rpm) for 30 min sedimented the precipitate. The supernatant was decanted and the pellet was again dissolved in acetone (20 mL) at 30° C. Precipitation, sedimentation and decanting were performed as previously described. A third cycle of acetone precipitation and sedimentation was performed and after decanting the supernatant, the pellet was frozen at −80° C. and then dried to constant mass under high vacuum to give PEG reagent 1 as an off-white solid (227 mg). $^1$H NMR (CDCl$_3$): δ (ppm) 2.49 (s, 6H), 3.38 (s, 6H), 3.45-3.86 (m), 4.33 (m, 1H), 7.36 (AA'BB', 4H), 7.64 (AA'BB', 2H), 7.68 (AA'BB', 4H), 7.83 (AA'BB', 2H).

EXAMPLE 2

Comparison of the Reactivity of PEG Reagents 1 and 2 with a Human IgG, Fab Fragment In this example, PEG reagent 1 of Example 1 was compared with the following reagent, PEG reagent 2, in which MPEG is $CH_3O.(CH_2CH_2O)_{m-1}$—$CH_2CH_2$—, of Cong et al., supra.:

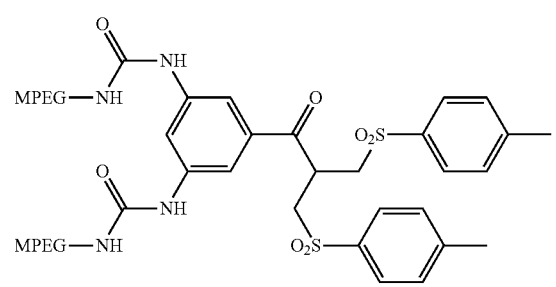

Figures 1, 2:
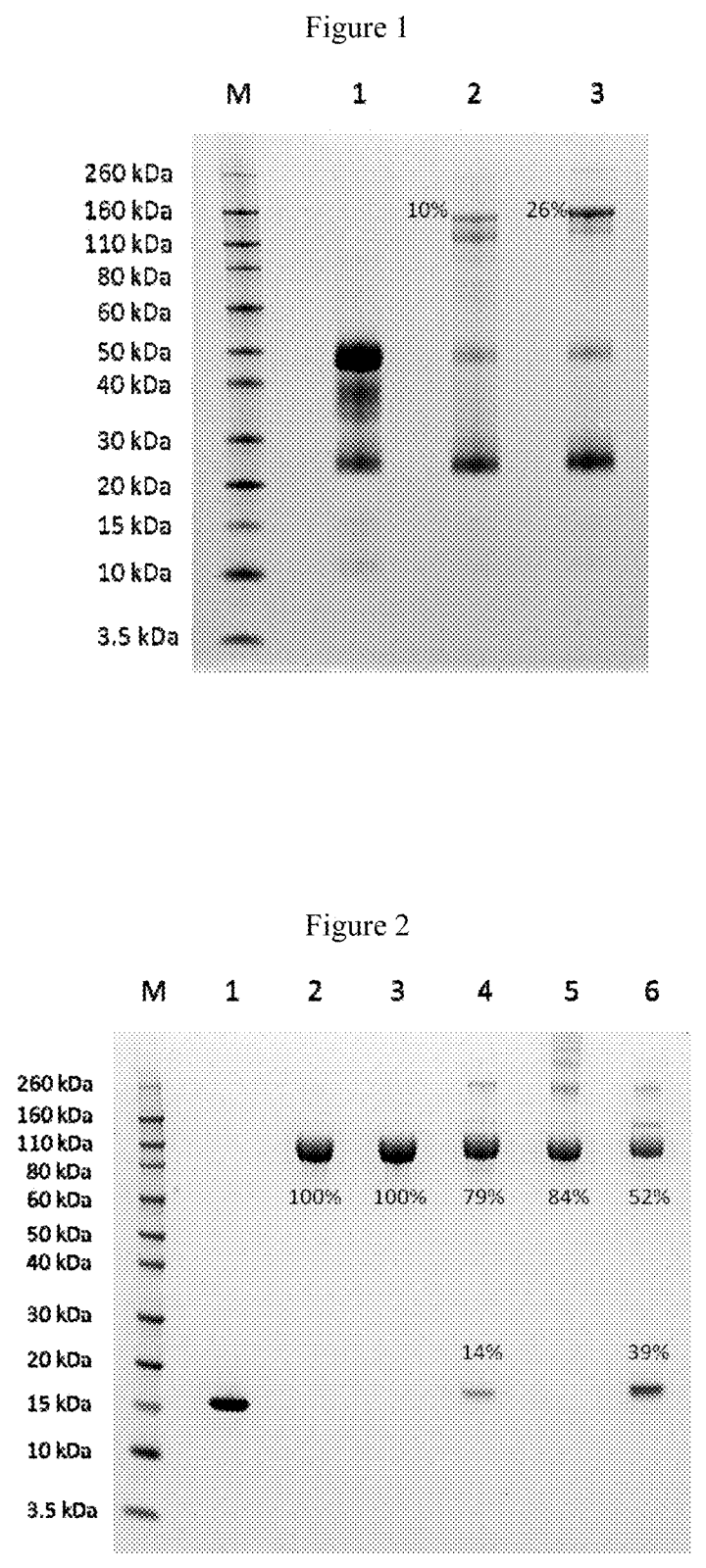

A human IgG, Fab fragment solution (4.0 mg, 0.909 mL) Jackson ImmunoResearch Laboratories Inc. Cat. No. 009-000-007) was diluted to 4.95 mL with 50 mM sodium phosphate, pH 7.4 (containing 150 mM NaCl and 20 mM EDTA). To the Fab fragment solution, 1.0 M DTT (50 μL) was added to give a final DTT concentration of 10 mM in order to reduce the interchain disulfide bond so that PEGylation could occur. The resulting solution was mixed gently and then stood at 4° C. for 1 h. The solution of reduced Fab was buffer exchanged into 50 mM sodium phosphate, pH 7.4 (containing 150 mM NaCl and 20 mM EDTA) using PD-10 desalting columns. The reduced Fab solution was split equally into two portions (3.5 mL, ~2 mg). Two PEG reagents: PEG reagent 1 and PEG reagent 2, were dissolved in 50 mM sodium phosphate, pH 7.4 (containing 150 mM NaCl and 20 mM EDTA) at 20 mg/mL. To the first portion of Fab solution, PEG reagent 1 (75 µL, 1.5 mg) was added and to the second portion of Fab solution, PEG reagent 2 (75 µL, 1.5 mg) was added. Both reactions were mixed gently and then stood at 4° C. for 20 h. After 20 h the crude reaction mixtures were analysed by SDS-PAGE. The gel was stained with INSTANTBLUE™ and imaged using an IMAGEQUANT™ LAS 4010 instrument. The result is shown in FIG. 1. In FIG. 1, lane M indicates Novex Protein Standards; lane 1 indicates human IgG, Fab fragment; lane 2 indicates PEGylated product from PEG reagent 2 at 20 h; and lane 3 indicates PEGylated product from PEG reagent 1 at 20 h. From the SDS-PAGE analysis it can be seen that, while both PEG reagents 1 and 2 were successfully conjugated to the Fab fragment, the efficiency of the conjugation for PEG reagent 1 was 26%, over double of that for PEG reagent 2 (10%).

EXAMPLE 3

Stability Comparisons of IFN α-2a Conjugates Prepared with PEG Reagents 1 and 2

Preparation of Conjugates

A solution of IFN α-2a (6.5 mg, 0.845 mg/mL) was prepared in 50 mM sodium phosphate buffer, pH 7.4 (containing 150 mM NaCl and 20 mM EDTA). The protein solution was diluted with buffer (313 µL) and a 1.0 mM DTT solution in water (187.5 mL) was then added to give a final DTT concentration of 25 mM and a reaction volume of 7.5 mL. After gentle mixing, the reaction was stood at room temperature for 30 min. The reduced protein was buffer exchanged into 50 mM sodium phosphate, pH 7.4 (containing 150 mM NaCl and 20 mM EDTA) using PD-10 columns. The eluted protein solution was centrifuged (3000 g, 4° C., 5 min) and the supernatant was then quantified by UV absorbance measurements at 280 nm (0.532 mg/mL). The protein solution was diluted to 0.10 mg/mL with buffer. PEGs 1 and 2 were dissolved at 20 mg/mt in 50 mM sodium phosphate, pH 7.4 (containing 150 mM NaCl and 20 mM EDTA). Two vials were each charged with reduced IFN α-2a (2.5 mg, 24.8 mL); to the first vial PEG reagent 1 (4.9 mg, 0.245 mL) was added and to the second vial PEG reagent 2 (4.9 mg, 0.245 mL) was added. The reactions were mixed gently and then stood at 4° C. for 18 h. Any reduced protein in the final reaction mixtures was oxidised by sequentially adding 5 mg/mL copper sulfate (12.18 µL) and then 50:50 (mM) GSH/GSSG (0.25 mL). The reoxidation reaction was conducted at 4° C. overnight. The reaction mixtures were diluted ×4 with 100 mM sodium acetate, pH 4 and then purified by cation exchange chromatography (MACRO-CAP™ SP) using a step gradient elution of 100 mM sodium acetate, pH 4 (1.0 M NaCl) with the desired conjugates eluting at 0.60-0.65 M NaCl.

Stability Comparison 1. Stress Tests for IFN α-2α Conjugates Prepared with PEG Reagents 1 and 2:

For each of the IFN α-2a samples PEGylated with 1 and 2 (in filter sterilised PBS), four vials were prepared. Each vial was loaded with 20 µL of conjugate at a concentration of 200 µg/mL. Two vials for each of the test samples contained 10 mM DTT. One vial with and one vial without DTT were heated to 50° C. for 1 h. The remaining vials were heated to 90° C. for 10 min. The samples (along with unconjugated protein and unstressed conjugate) were analysed by SDS-PAGE—the gels were stained with INSTANTBLUE™ and imaged using an IMAGEQUANT™ LAS 4010 instrument and the results are shown in FIGS. 2 and 3 for PEG 1-IFN α-2a and PEG 2-IFN α-2a respectively. In FIGS. 2 and 3, lane M indicates Novex Protein Standards; lane 1 indicates IFN α-2a; lane 2 indicates PEG-IFN α-2a; lane 3 indicates PEG-IFN α-2a—50° C., 1 h; lane 4 indicates PEG-IFN α-2a—50° C., DTT, 1 h; lane 5 indicates PEG-IFN α-2a—90° C., DTT, 10 min; and lane 6 indicates PEG-IFN α-2a—90° C., DTT, 10 min.

FIGS. 2 and 3 show that both of the conjugates tested were stable at 50° C. for 1 h. However, after heating at 50° C. for 1 h in the presence of 10 mM DTT, significantly more free protein and aggregation is observed for the conjugate prepared with PEG reagent 2. Thermal stress at 90° C. for 10 min resulted in release of free protein for the conjugate PEGylated with 2 but not for the conjugate PEGylated with 1.

Stability Comparison 2. 28 Day, 40° C., Accelerated Stability Studies for IFN α-2a Conjugates PEGylated with PEG Reagents 1 and 2.

Figure 4:
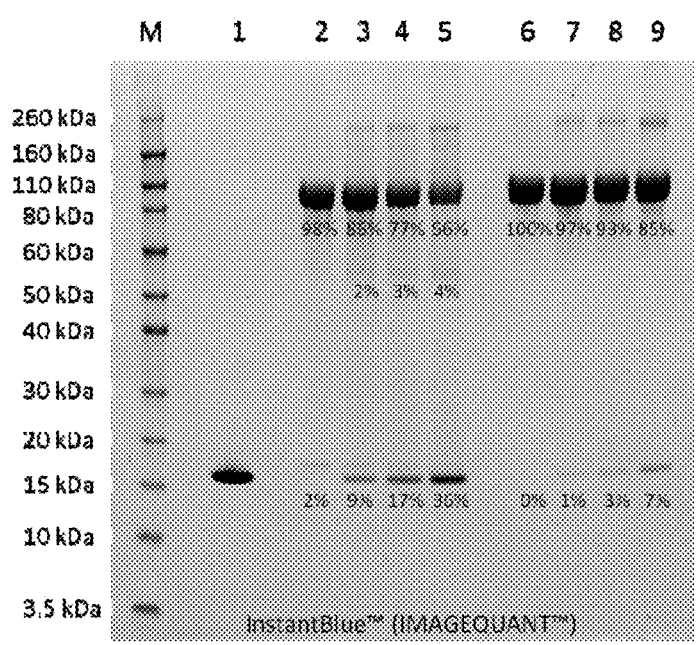

Solutions of the two test samples were made up in filter sterilised PBS (containing 0.01% (w/v) NaN$_3$) at a protein concentration of 200 µg/mL. For each of PEG 1-IFN α-2a and PEG 2-IFN α-2a four vials were loaded with 100 µL of test sample. One vial for each sample was immediately frozen at −80° C. (t=0 days). The remaining three were sealed with PARAFILM® and then were stored at 40° C. At 7, 14 and 28 days a sample was removed from storage and frozen at −80° C. until the completion of the study. The test samples were flash thawed in a water bath thermostated at 37° C. and analysed by SDS-PAGE (INSTANTBLUE™ stained and imaged using an IMAGEQUANT™ LAS 4010 instrument) and the result is shown in FIG. 4, in which lane M indicates Novex Protein Standards; lane 1 indicates IFN α-2a (1 µg); lane 2 indicates PEG 2-IFN α-2a, Day 0; lane 3 indicates PEG 2-IFN α-2a, Day 7; lane 4 indicates PEG 2-IFN α-2a, Day 14; lane 5 indicates PEG 2-IFN α-2a, day 28; lane 6 indicates PEG 1-IFN α-2a, Day 0; lane 7 indicates PEG 1-IFN α-2a, Day 7; lane 8 indicates PEG 1-IFN α-2a, Day 14; lane 6 indicates PEG 1-IFN α-2a, Day 28. In FIG. 4, it can clearly be seen that the PEG 2-IFN α-2a is less stable than PEG 1-IFN α-2a with more free protein and less conjugate remaining at each time point.

EXAMPLE 4

Conjugation of IFN-β-1b with PEG Reagent 1

Figure 5:
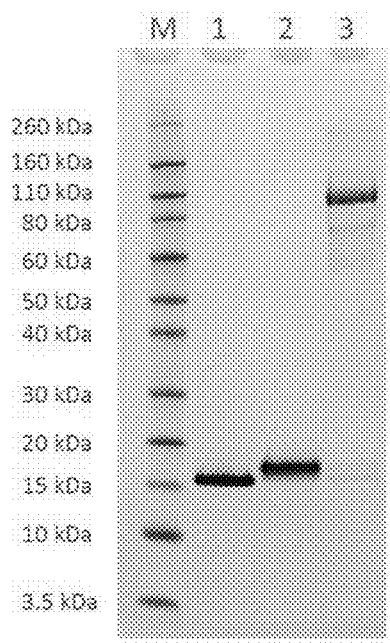
FIG. 5 illustrates the SDS-PAGE gel obtained in Example 4.

To disulfide reduced IFN-β-1b (9.5 mg, 0.3 mg/mL) at pH 7.3 was added a solution of PEG reagent 1 (1.7 mL, 20 mg/mL) at pH 7.3. The resulting solution was allowed to incubate at 22° C. for 4 h, whereupon the crude reaction mixture was analysed by SDS-PAGE. The gel was stained with INSTANTBLUE™ and imaged using an IMAGEQUANT™ LAS 4010 instrument. The result is shown in FIG. 5. In FIG. 5, in lane M are Novex protein standards; lane 1 is the starting IFN-β-1b; lane 2 is the reduced IFN-β-1b and lane 3 is the reaction mixture of PEG reagent 1 with IFN-β-1b. From the SDS-PAGE analysis it can be seen that PEGylation of IFN-β-1b occurred successfully with a product band visible level with the 110 kDa protein standard.

EXAMPLE 5

Preparation of Branched PEG Reagent 11

Step 1: Derivatisation of O-(2-aminoethyl)-O"-methyl(polyethylene glycol) with Fmoc-L-aspartic acid 4-tert-butyl ester

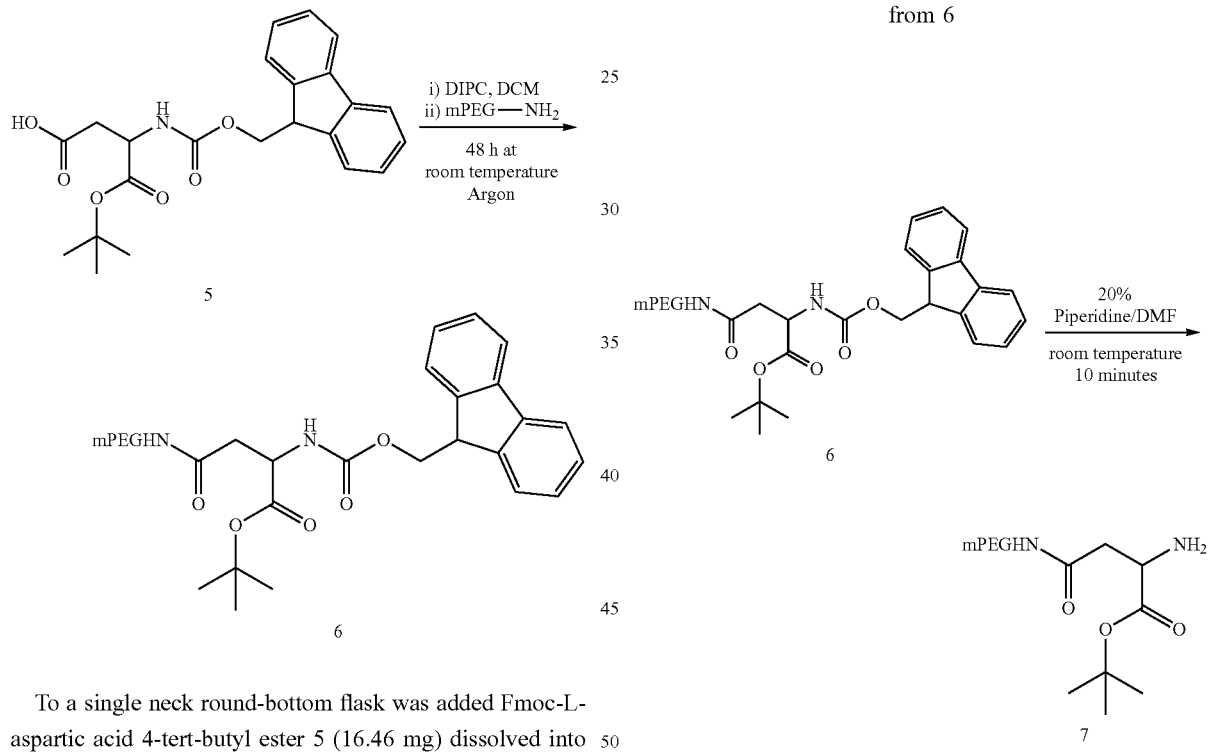

To a single neck round-bottom flask was added Fmoc-L-aspartic acid 4-tert-butyl ester 5 (16.46 mg) dissolved into anhydrous dichloromethane (DCM) (5 mL). Fresh N,N'-diisopropylcarbodiimide (DIPC) (6.3 μL) was added and the reaction mixture was allowed to stir, at room temperature for 30 min. O-(2-aminoethyl)-O"-methyl(polyethylene glycol) 10 (100 mg) was placed separately in a one neck 50 mL schlenk flask fitted with a septum and a magnetic stir bar. Azeotropic distillation was carried out using 5 mL of toluene with the aid of an oil pump fitted with an ice trap to dry the polymer prior to the coupling reaction. Anhydrous DCM (5 mL) was added to the flask under argon atmosphere to dissolve the PEG completely. 4-Dimethylaminopyridine (DMAP) (1.22 mg) was added to the PEG solution. The activated aspartic derivative was injected into the PEG solution drop-wise. The resulting solution was allowed to stir for 48 h at room temperature under argon atmosphere. After this time, volatiles were removed by roto-evaporation and the crude product was placed under vacuum for 40 min. The crude was then re-dissolved in acetone and filtered through cotton-wool into a pre-weighed centrifuge tube. The sample was placed in dry-ice for precipitation to occur. The precipitate was isolated by centrifugation (−9° C., 4000 rpm, 30 min). The solid obtained was dried in a desiccator to afford a white-off product (89 mg)

$^1$H-NMR (CDCl$_3$, 400 MHz) δ/ppm: 1.45 (s, 9H), 2.6-2.8 (dd, 2H), 3.38 (s, 3H), 3.5-3.8 (broad, PEG), 4.22 (t, 1H), 4.41 (d, 2H), 4.50 (m, 1H), 5.94 (br, 1H), 6.79 (br, 1H), 7.31 (t, 2H), 7.40 (t, 2H), 7.56 (d, 2H), 7.77 (d, 2H)

Step 2: Removal of Fluorenylmethyloxycarbonyl from 6

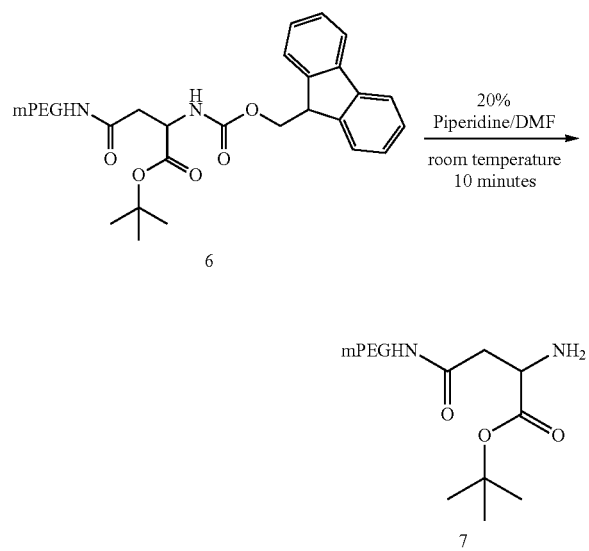

Aspartic PEG derivative 6 (50 mg) was dissolved in dimethylformamide (DMF) (0.8 mL) in a single neck round-bottom flask (Kocienski, 1994). Under magnetic stirring, a solution of piperidine (0.2 mL) was added drop-wise. The reaction mixture was allowed to stir at room temperature for 10 min. After this time, volatiles were removed by roto-evaporation and the crude product was dried under vacuum for 1 hour. The crude was then purified by the dry-ice precipitation method described in step 1. A white product was afforded after drying in a desiccator (44 mg). $^1$H-NMR (CDCl$_3$, 400 MHz) δ/ppm: 1.36 (s, 9H), 2.76-2.49 (dd, 2H), 3.31 (s, 3H), 3.5-3.8 (broad, PEG), 4.31 (t, 1H), 6.89 (br, 1H)

Step 3: Preparation of Mono-PEG Aspartic Derivative DB Reagent 8

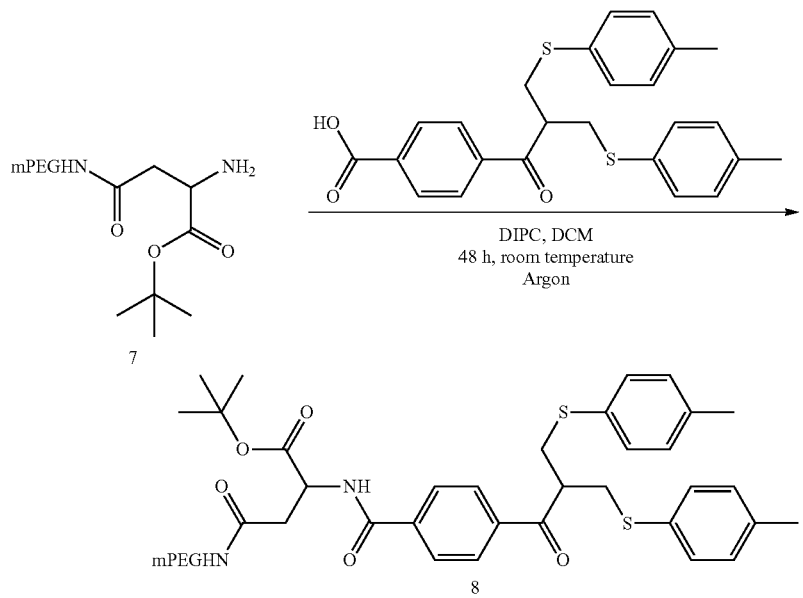

To a single neck round-bottom flask was added aspartic acid 4-tert-butyl ester PEG derivative 7 (90 mg) along with 5 mL of toluene, for azeotropic distillation. After complete dryness, anhydrous DCM (5 mL) was added to the flask under argon atmosphere to dissolve 7 completely. 4-Dimethylaminopyridine (DMAP) (1.1 mg) was added to the solution. In a separate flask, the disulfide-bridging linker (15.7 mg) was added and dissolved into anhydrous DCM (5 mL). Fresh N,N'-diisopropylcarbodiimide (DIPC) (4.5 mg, 5.31 μL) was added and the reaction mixture was allowed to stir, at room temperature for 30 min. The activated linker was then added to the PEG solution drop-wise. After a total reaction time of 48 h, volatiles are removed by rotoevaporation and the crude product was placed under vacuum for 40 min. Purification and isolation of product was achieved by the dry-ice precipitation method described in section Step 1. The solid obtained was dried in a desiccator to afford a white-off product (83.5 mg). $^1$H-NMR (CDCl$_3$, 400 MHz) δ/ppm: 1.43 (s, 9H), 2.33 (s, 6H), 2.62-2.91 (dd, 2H), 3.14-3.22 (m, 4H), 3.36 (s, 3H), 3.5-3.8 (br, PEG), 4.89 (t, 1H), 6.97 (br, 1H), 7.05 (d, 4H), 7.12 (d, 4H), 7.56 (d, 2H), 7.73 (d, 2H)

Step 4: Boc Group Removal from Mono PEG DB Aspartic Derivative 8

Aspartic PEG

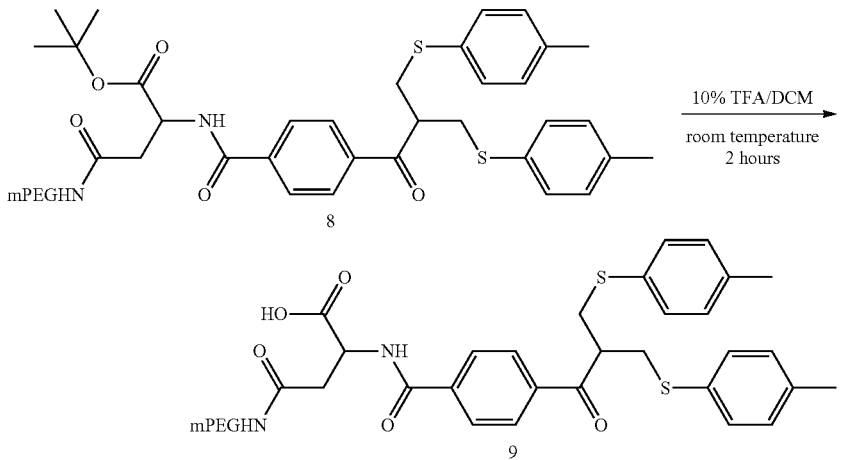

derivative 8 (50 mg) was dissolved in anhydrous DCM (0.9 mL) in a single neck round-bottom flask. Under magnetic stirring, a solution of trifluoroacetic acid (0.1 mL) was added drop-wise (Kocienski, 1994). The reaction mixture was allowed to stir at room temperature for 2 h. After this time, volatiles were removed by roto-evaporation and the crude product was dried under vacuum for 1 h. Isolation of product was achieved by the dry-ice precipitation method described previously in step 1. A white product was afforded after drying in a desiccator (39 mg). $^1$H-NMR (CDCl$_3$, 400 MHz) δ/ppm: 2.33 (s, 6H), 2.68 (m, 2H), 3.14-3.22 (m, 4H), 3.37 (s, 3H), 3.5-3.8 (broad, PEG), 4.97 (br, 1H), 7.05 (d, 4H), 7.12 (d, 4H), 7.59 (d, 2H), 7.77 (d, 2H)

Step 5: Preparation of Bis-PEG Aspartic DB Reagent 10

Anhydrous DCM (5 mL) was added to the flask under argon atmosphere to dissolve the PEG completely. 4-Dimethylaminopyridine (DMAP) (0.58 mg) was added to the PEG solution. The activated aspartic PEG derivative was added to the PEG solution drop-wise. The resulting solution was allowed to stir for 48 h at room temperature under argon atmosphere. After this time, volatiles were removed by roto-evaporation and the crude product was placed under vacuum for 40 min. The crude was re-dissolved in acetone for the purification by the dry-ice precipitation method described in step 1. The solid obtained was dried in desiccator to afford a white-off product (79 mg). The same

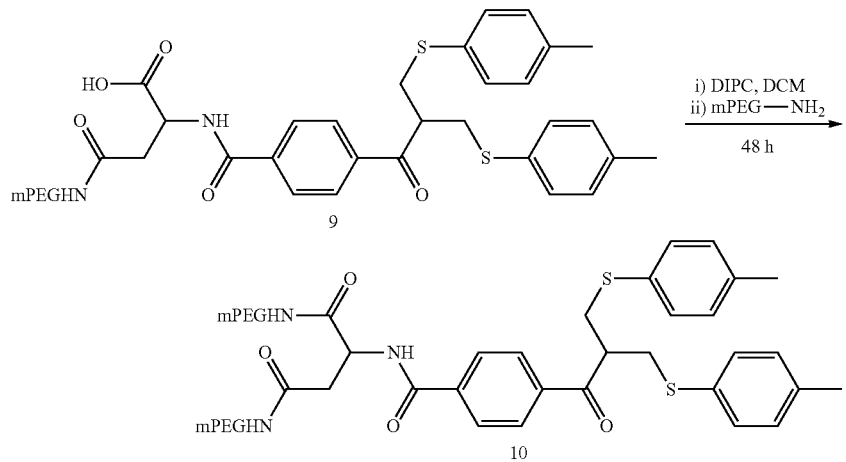

Aspartic PEG 10 kDa derivative 9 (50 mg) was dissolved in toluene (5 mL) for azeotropic distillation. Fresh N,N'-diisopropylcarbodiimide (DIPC) (2.4 mg, 2.79 μL) was added and the reaction mixture was allowed to stir, at room temperature for 30 min. O-(2-aminoethyl)-O''-methyl(polyethylene glycol) (PEG) 10 kDa (47.4 mg) was placed separately in a one neck 50 mL schlenk flask fitted with a septum and a magnetic stir bar. Azeotropic distillation was carried out using 5 mL of toluene, as previously described procedure was applied for the preparation of bis-PEG aspartic DB reagent 2×20 kDa. $^1$H-NMR (CDCl$_3$, 400 MHz) δ/ppm: 2.34 (s, 6H), 2.68-2.93 (m, 2H), 3.14-3.22 (m, 4H), 3.37 (s, 3H), 3.5-3.8 (broad, PEG), 4.94 (br, 1H), 7.05 (d, 4H), 7.12 (d, 4H), 7.61 (d, 2H), 7.86 (d, 2H)

Step 6: Oxidation of Bis-Sulfide to Bis-Sulfone

Scheme 1.6 - Reaction scheme for the oxidation of the sulfate groups to sulfones

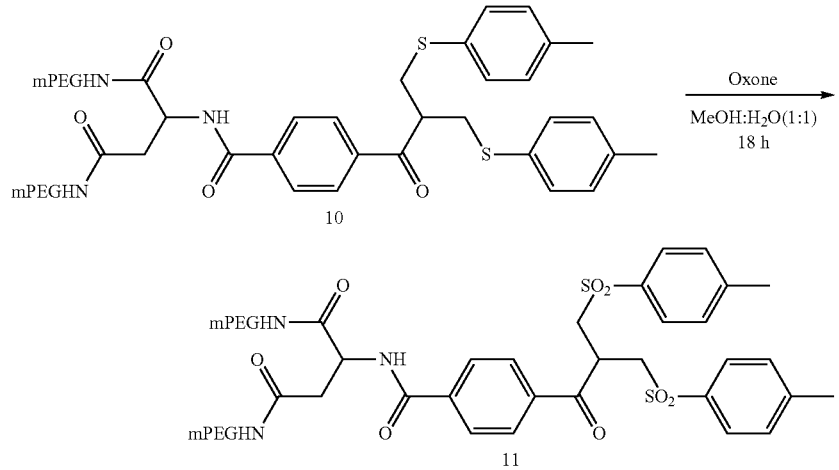

Bis-PEG aspartic DB reagent 10 (20 mg) was dissolved in an aqueous solution of 50% methanol (3 mL) in a 15 mL centrifuge tube. A magnetic stirrer bar was added and while under agitation, OXONE® (potassium peroxymonosulfate) was added to the solution. The reaction mixture was allowed to stir over-night, at room temperature. After this time, the solution was transferred to a 50 mL round-bottom flask and volatiles were removed by roto-evaporation. Purification of crude product was achieved by dry-ice precipitation method described in step 1. The solid obtained was dried in a desiccator to afford a white-off product (16.2 mg). $^1$H-NMR (CDCl$_3$, 400 MHz) δ/ppm: 2.46 (s, 6H), 2.68 (m, 2H), 3.14-3.22 (m, 4H), 3.37 (s, 3H), 3.5-3.8 (broad, PEG), 4.97 (br, 1H), 7.35 (d, 4H), 7.59 (d, 6H), 7.77 (d, 2H).

EXAMPLE 6

Preparation of PEG Reagent 13 decanting the supernatant, the pellet was frozen at −80° C. and then dried to constant mass under high vacuum to give PEG reagent 13 as a white solid (93 mg). $^1$H NMR (CDCl$_3$): δ (ppm) 2.42 (s, 6H), 3.39 (s, 6H), 3.46-3.84 (m), 4.34-4.38 (m, 1H), 7.05 (s, 1H), 7.36 (AA'BB', 4H), 7.64 (AA'BB', 2H), 7.68 (AA'BB', 4H), 7.83 (AA'BB', 2H).

EXAMPLE 7

Conjugation of PEG Reagent 13 to a Fab

A solution of a trastuzumab derived Fab (2.6 mg/mL, 2.5 mL) was buffer exchanged, using a PD-10 desalting column (GE Healthcare), into 50 mM sodium phosphate buffer, pH 7.4 (containing 150 mM NaCl and 20 mM EDTA). The resulting solution was then treated with DTT (1 M, 35 µL, 1 h, 4° C.) to reduce the interchain disulfide of the Fab. The disulfide reduced Fab solution was then buffer exchanged into 50 mM sodium phosphate buffer, pH 7.4, using two

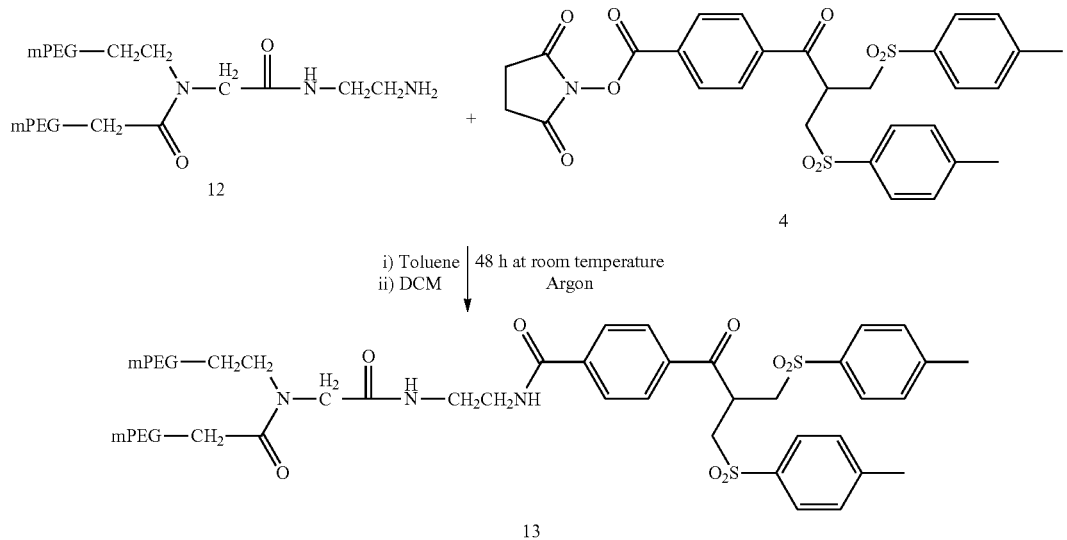

Figure 6:
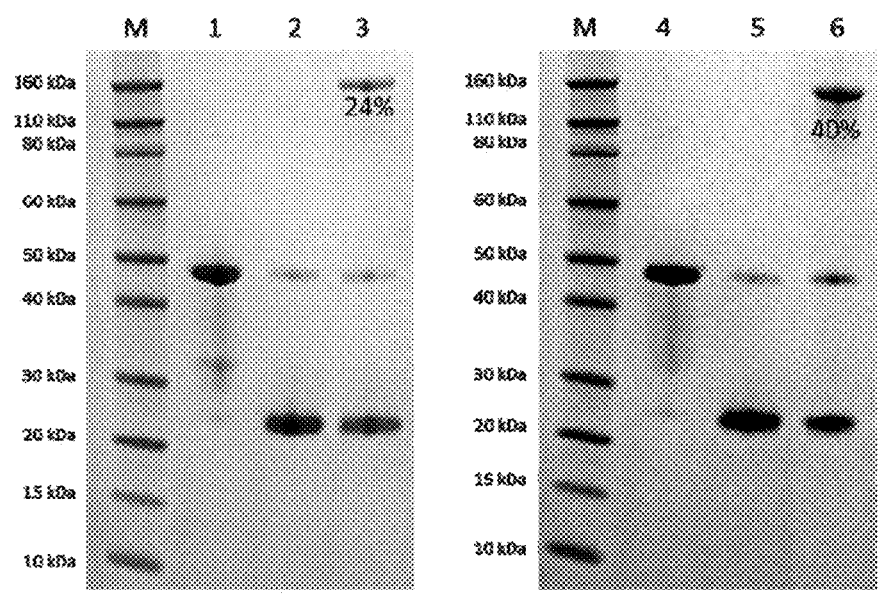
FIG. 6 illustrates the SDS-PAGE gels obtained in Example 7.

To a single neck round-bottomed flask containing a magnetic stirrer bar, was added bifurcated PEG amine 12 (100 mg, 40 kDa, JenKem Technology, code Y—NH2-40K, lot ZZ099P120) and toluene (8 mL). The resulting homogeneous solution was evaporated under reduced pressure using a rotary evaporator for 0.5 h to leave a solid residue. The residue was dissolved in dichloromethane (3 mL), the flask was sealed with a septum and the mixture stirred under argon. To the solution was added compound 4 (8.4 mg), the flask was resealed with a septum and the reaction was stirred at room temperature for 48 h. The septum was removed and the volatile portion was removed via evaporation under reduced pressure using a rotary evaporator. Acetone (10 mL) was added to the residue and the solid was dissolved with gentle warming (30° C.). The resulting solution was filtered through non-absorbent cotton wool into a 15 mL Falcon tube. Cooling the solution in a dry-ice bath resulted in a thick precipitate. Centrifugation (−9° C., 4000 rpm) for 30 min sedimented the precipitate. The supernatant was decanted and the pellet was again dissolved in acetone (10 mL) at 30° C. Precipitation, sedimentation and decanting were performed as previously described. A third cycle of acetone precipitation and sedimentation was performed and after PD-10 desalting columns. Two aliquots of the solution were then taken, each containing 1 mg of Fab. One aliquot was stored at 4° C. and the other at room temperature (RT). A solution of PEG reagent 13 was prepared in 50 mM sodium phosphate buffer, pH 7.4 (5 mg/mL) and 175 µL of the solution was added to each of the reduced Fab solutions. Each of the solutions was diluted, so that final Fab concentration was 0.5 mg/mL. The reaction solutions were shaken gently before being allowed to stand for 20 h. After 20 h, the samples (along with starting Fab and reduced Fab samples) were analysed by SDS-PAGE—the gels were stained with INSTANTBLUE™ and imaged using an IMAGEQUANT™ LAS 4010 instrument. The results are shown in FIG. 6. In FIG. 6, the lane labelled M shows Novex Protein Standards; lanes 1 and 4 show the starting non-reduced Fab; lanes 2 and 5 show the reduced Fab; lane 3 shows the 4° C. reaction mixture and lane 6 shows the room temperature reaction mixture. From the SDS-PAGE analysis it can be seen that PEG reagent 13 conjugated successfully to the Fab fragment, the efficiency of the conjugation at 4° C. was 24%, and at room temperature the efficiency was 40%.

The invention claimed is:
1. A compound having general formula:

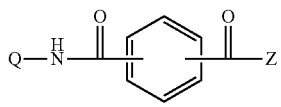

in which Q is:

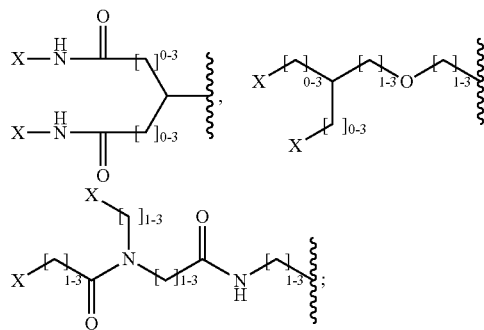

each X independently represents a polymer chain; and Z represents either —CH.(CH$_2$L)$_2$ or —C(CH$_2$L)(=CH$_2$), in which each L independently represents a leaving group.

2. A compound as claimed in claim 1, in which each X represents a poly(alkylene glycol), polyvinylpyrrolidone, polyacrylate, polymethacrylate, polyoxazoline, polyvinylalcohol, polyacrylamide, polymethacrylamide, HPMA copolymer, polyester, polyacetal, poly(ortho ester), polycarbonate, poly(imino carbonate), polyamide, or polysaccharide.

3. A compound as claimed in claim 1, in which each L independently represents —SR, —SO$_2$R, —OSO$_2$R, —N$^+$R$_3$, —N$^+$R$_2$, —N$^+$H$_2$R, halogen, or —OØ, in which R represents a hydrogen atom or an alkyl, aryl or alkyl-aryl group, and Ø represents a substituted aryl group containing at least one electron withdrawing substituent.

4. A compound as claimed in claim 3, in which each L independently represents phenylsulfonyl or tosyl.

5. A compound, said compound having the formula:

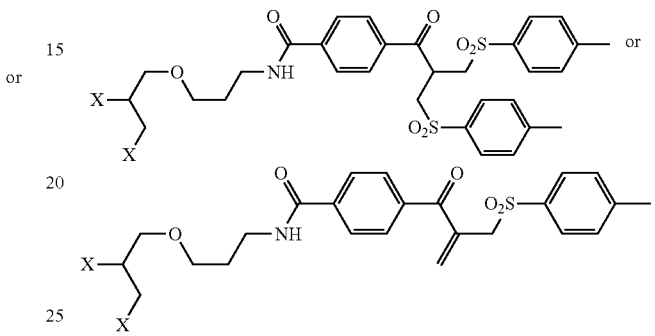

in which each X independently represents a polymer chain.

6. A compound as claimed in claim 5, in which each X independently represents polyethylene glycol of the formula CH$_3$O—(CH$_2$CH$_2$O)$_m$— in which m is the number of ethylene oxide units in X.

* * * * *